(12) United States Patent  (10) Patent No.: US 8,192,025 B2
Peyman  (45) Date of Patent: Jun. 5, 2012

(54) NON-CONTACT OPTICAL COHERENCE TOMOGRAPHY IMAGING OF THE CENTRAL AND PERIPHERAL RETINA

(76) Inventor: Gholam A. Peyman, Sun City, AZ (US)

( * ) Notice: Subject to any disclaimer, the term of this patent is extended or adjusted under 35 U.S.C. 154(b) by 0 days.

(21) Appl. No.: 13/279,584

(22) Filed: Oct. 24, 2011

(65) Prior Publication Data

US 2012/0092616 A1 Apr. 19, 2012

Related U.S. Application Data

(63) Continuation-in-part of application No. 12/492,491, filed on Jun. 26, 2009, now Pat. No. 8,070,289.

(51) Int. Cl.
*A61B 3/14* (2006.01)
*A61B 3/10* (2006.01)
(52) U.S. Cl. ......... 351/206; 351/213; 351/220; 351/221
(58) Field of Classification Search .................. 351/205, 351/206, 213, 220, 221
See application file for complete search history.

(56) References Cited

U.S. PATENT DOCUMENTS

| | | | |
|---|---|---|---|
| 5,252,998 | A | 10/1993 | Reis et al. |
| 5,491,524 | A | 2/1996 | Hellmuth et al. |
| 6,337,920 | B1 | 1/2002 | Muhlhoff |
| 6,585,374 | B2 | 7/2003 | Matsumoto |

*Primary Examiner* — Ricky Mack
*Assistant Examiner* — Mahidere Sahle
(74) *Attorney, Agent, or Firm* — Wenderoth, Lind & Ponack, L.L.P.

(57) ABSTRACT

A system includes a mirror having an axis extending through a central portion thereof, and a portion of the mirror being configured to repeatedly oscillate between a first position and a second position around the axis, so as to record a field of up to 200 degrees of a portion of the central and peripheral retina, a first scanner configured to use a spectral domain optical coherence tomography system to obtain a non-contact wide angle optical coherence tomography-image of the portion of the central and peripheral retina, and a second scanner configured to obtain an image of the retina, wherein the mirror is configured to oscillate so as to move the focal point of the mirror from one side of a pupil to another side, thereby permitting scanning light inside the eye to cover a predetermined peripheral field, thus creating a two dimensional or three dimensional image of the field.

20 Claims, 3 Drawing Sheets

NON-CONTACT OPTICAL COHERENCE TOMOGRAPHY IMAGING OF THE CENTRAL AND PERIPHERAL RETINA

CROSS REFERENCE TO RELATED APPLICATION

This application is a continuation-in-part of U.S. application Ser. No. 12/492,491, filed Jun. 26, 2009, now U.S. Pat. No. 8,070,289 the entirety of which is incorporated herein by reference.

BACKGROUND

1. Field of Invention

The present invention relation to a system for Non-contact Optical Coherence Tomography (OCT) imaging of the central and peripheral retina.

2. Related Art

Ophthalmic Optical Coherence Tomography (OCT) of the eye was originally developed by obtaining cross-sectional images of the sensory retina and retinal pigment epithelium. Recently, spectral domain OCT became available, a new technique that allowed major improvements particularly regarding image acquisition speed and image resolution. However, existing instruments do not scan the retinal periphery. The OCT scan is typically restricted to the central <40° of the retina.

OCT is presently used (in ophthalmology) to evaluate only either the thickness of the central retina in macular diseases or separately the status of the optic nerve head in glaucoma patients. Furthermore obtaining the OCT pictures require dilatation of the pupil prior to taking pictures. OCT can not be performed in patients with a constricted pupil; since presently available optics do not permit it. In convention systems, the existing unbearable reflexes created by their optical elements make it impossible for the operator to simultaneously see the retina and focus on the desired area (e.g., the macula or the Optic Nerve head). In addition, the field of view is very limited; thus, important regions in the peripheral retina can not be visualized with current OCT systems and the system needs a skilled personal to handle the instrument.

Present OCT systems generally employ a Fundus Camera Design. A fundus camera is a complex optical system for imaging and illuminating the retina. Due to its location the retina must be imaged and illuminated simultaneously by using optical components common to the imaging and illumination system.

Conventional Fundus Cameras used for OCT generally include an objective lens which forms an intermediate image of the retina in front of a zoom lens, designed to accommodate for the refractive error of the patient, which relays the intermediate image to the CCD. Light travels through the objective lens in both directions making the consideration of back reflections important. On the illumination side, the objective lens images an annular ring of light onto the pupil; therefore, the need for dilation of the pupil. This ring of light then disperses to give a near uniform illumination of the interior retinal surface. The objective lens also serves a role in the imaging optics. It captures pencils of light emanating from the eye and forms an intermediate image of the retina. This intermediate image is then relayed by additional optics to a digital imaging sensor or film plane.

The objective lens also serves as the limiting factor in the field of view of the camera. FIG. 1 shows the relationship between the objective lens and the eye.

Bundles of rays leaving the periphery of the retina emerge from the emmetropic eye as a roughly collimated bundle of rays. This bundle must pass through the edge of the objective lens in order to become part of the fundus image. Bundles coming from more eccentric points on the retina cannot be captured by the objective and therefore cannot be seen in the fundus image. One method of increasing the field of view in this conventional configuration is to increase the size of the objective lens as seen in FIG. 2.

However, increasing the diameter of the objective lens causes an increase in the aberration of these lenses with size. Current practical limits taking this approach lead to a roughly 40-degree field of view seen in modern fundus cameras. An alternative method for increasing the field of view is to move the objective lens closer to the eye which has also its own limitations. The extreme case for this technique is where a portion of the objective lens actually comes in contact with the cornea. One drawback to this configuration is patient aversion due to the proximity of the lens, and increased risk of infection and corneal abrasion.

SUMMARY OF THE INVENTION

The embodiments of the present invention overcome the above problems with the conventional systems.

One objective of the present invention is to develop a non-contact wide field OCT system to extend the field of view >200 degree and can be performed in un-dilated pupil.

This invention can provide access to the retinal periphery and simplifies taking images. These sections of the retinal periphery may provide important information about the diseased areas of the peripheral retina permitting evaluation and potential treatment. Additionally, the present invention enables ophthalmologists to visualize and diagnose a variety of ailments including glaucoma, macular degeneration, retinal detachment, and diabetic retinopathy and all peripheral retinal diseases. The OCT system of the present invention can utilize low coherent visible or preferably infra red wave lengths of up to 10640 nm. The OCT system of the present invention can also makes a patient's examination easier by eliminating the time spent to dilate the patients pupil and reducing the focusing time, which improves the patient's tolerance of the procedure since a wide-field fundus photograph can be generated with the same infrared light without blinding the patient with visible light.

In conventional systems no information can be obtained from the vitreoretinal interface in the retinal periphery which is main cause of retinal tear and retinal detachment which is one of the main cause of blindness more frequently in near sighted patients. What is needed is a wide-field retinal imaging OCT system that extends the fields of view >200 degree field.

Additional features and advantages are described herein, and will be apparent from, the following Detailed Description and the figures.

DETAILED DESCRIPTION OF THE INVENTION

Embodiments of the present invention may include imaging modalities, such as optical coherence tomography, snapshot imaging Polarimetry and computed tomography imaging spectrometer. Additionally, White Light LED, infra red diodes, Nd—YAG as an illumination source, can each maintain excellent image quality across the field of view.

Spectral Domain Optical Coherence Tomography, OCT, operates in substantially the same manner as a low coherence Michelson interferometer. That is, light from a broadband source is separated into a reference and sample arm. Reflected light from both arms is recombined in the detection arm to form interference fringes when the optical path difference between sample and reference arms is within the coherence length of the source. The signal produced by the detection of interference fringes is proportional to the backscatter from the depth structure of the sample. Spectral components of the light in the detector arm are separated by a spectrometer allowing for the detection of interference fringes at different wavelengths corresponding to different optical path differences representing depth information. Structural depth information from the sample is recovered by a Fourier Transform of the spectral data allowing for optical sectioning of the sample. Swept Source OCT operates by replacing a broadband source with a rapidly scanning source that sweeps across a large range of wavelengths. The detector records the backscattered signal for each wavelength and position. By utilizing this methodology the recovered signal is equivalent to Spectral Domain OCT. Swept Source OCT allows for faster axial scanning than conventional Spectral Domain OCT and eliminates the need for a high performance spectrometer. Light from the swept source is coupled into a fiber coupler that separates the light into the reference and sample arms of the OCT system. The reference arm of the OCT system consists of a collimating lens, a block of material for compensating the material dispersion of the source and fixed mirror. Light entering the reference arm is collimated, passes through the dispersion compensating material is reflected by the fixed mirror back through the dispersion compensating material and is coupled into the fiber coupler. The sample arm of the system, responsible for imaging the retina, consists of scan mirrors, an afocal relay, a wide field of view through a concave and or elliptic mirror and subject's eye. The Oct images can be also converted into two dimensional of the retina by the computer soft ware.

Figure 3:
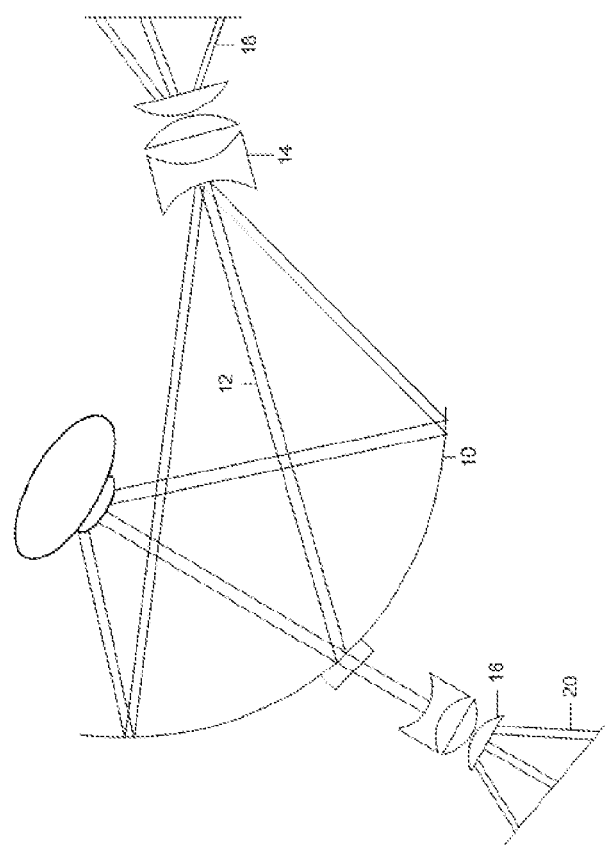
FIG. 3 illustrates an embodiment of the present invention in which the mirror is configured, if needed, to wobble or rotate around the visual axis.

The embodiments of the present invention may utilize a concave mirror 10 (circular or elliptical) that focuses a beam of light 12 toward its focal point located inside the patient's pupil (of 2-6 mm or larger diameter). The beam scanner and receivers are attached to the mirror. As shown in FIG. 3, the mirror can, if needed wobble, (or oscillate) slightly. This wobbling moves the focal point of the mirror slightly from one side of the pupil to the other side permitting the scanning light (low coherent wave lengths etc.) inside the eye to cover a larger peripheral field than possible without oscillation. Because the oscillation of the beam can be >1000× faster than the oscillation of the mirror, an expanded retinal field may be achieved, even if some of the beam is clipped by the pupil.

It is generally not possible to wobble (i.e., oscillate) rapidly a heavy fundus camera, nor would such wobbling significantly move the camera's view inside the eye. Additionally, a strip of an elliptical can be rotated along its axis if an emitter is attached to the mirror. This rotation may eliminate the need of an emitter oscillating in a circular fashion, since the elliptical mirror can rotate 360 degree thus covering the entire field of fundus.

Figure 2:
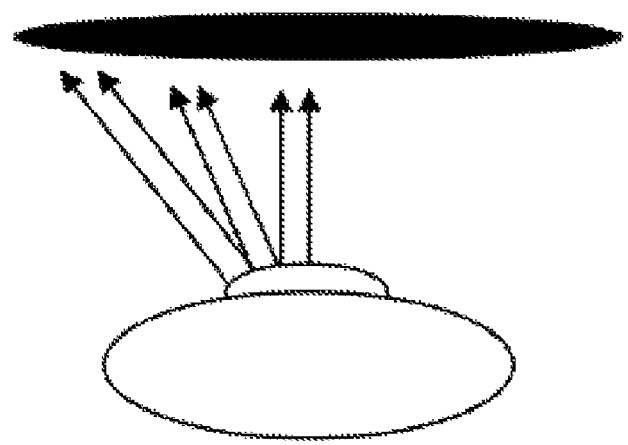
FIG. 2 illustrates an objective lens having an increased diameter.
Figure 1:
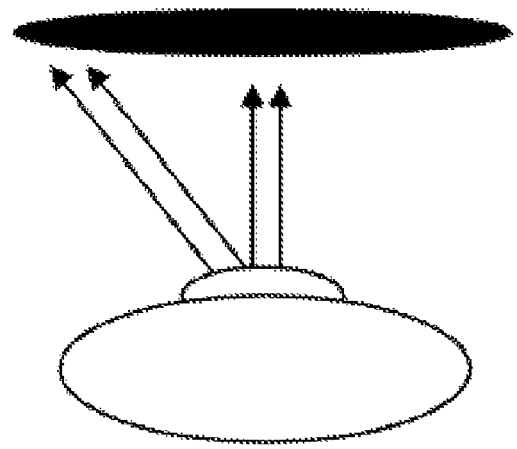
FIG. 1 illustrates a conventional objective lens positioned adjacent an eye.
Figure 4:
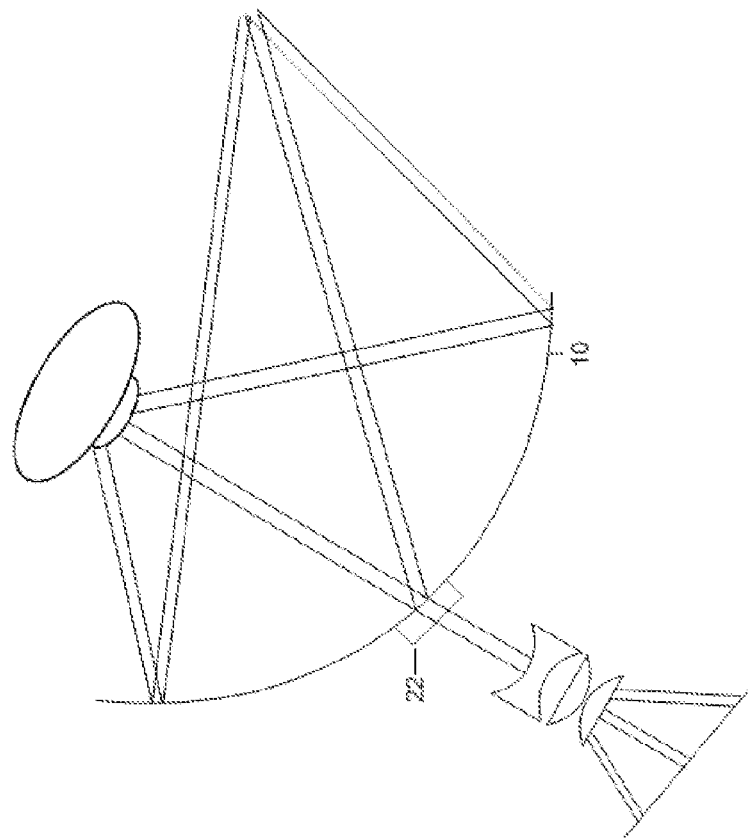
FIG. 4 illustrates an embodiment of the present invention in which a central part of the mirror can be switched automatically to achieve the beam diversion see attached.

Embodiments of the present invention also can have two emitters 14 and 16 and receiver arms 18 and 20 positioned in different areas with respect to the above mentioned concave mirror (FIG. 3). In these embodiments, a central OCT may be easily achieved, and then can be rapidly switched to a larger peripheral one. Both are preferably attached to the concave mirror 10, one central in front of the pupil for central scanning alone and one peripheral where the beam is reflected off the concave mirror before entering in the eye. These two arms 18 and 20 can be switched from one to the other electronically or manually, if desired. As illustrated in FIG. 4, a small central part 22 of the mirror 10 can be switched automatically to achieve the beam diversion. However, if desired the peripheral arm can be used alone.

Light entering the sample arm can be collimated and directed to a scan mirror responsible for sweeping the beam along the x axis. An afocal relay can direct the beam deflected by the x axis scan mirror to another scan mirror responsible for sweeping the beam along y axis. The y axis scan mirror can direct the beam to a wide field of view of a concave mirror or an elliptical mirror positioned in front of the subject's eye. This combination of scan mirrors, afocal relay and a wobbling-rotateable concave mirror or an elliptical mirror placed in front of the patients eye and an OCT system allows for three dimensional volumetric image acquisition over 200 degree field of the retina. Light incident to the retina is back scattered by retinal structures and propagates back through the scanning system and coupled into the fiber coupler. Light from the reference and sample arms is combined in the detection arm of the system producing interference fringes at the detector. Detection of the interference fringes is synchronized with the propagation of the specific wavelength coupled in the system by the swept source and the position of the x and y axis scan mirrors provides the desired wide angle OCT of the, central and peripheral retina. This method provides not only information on the retinal structure (thickness, degeneration, erosion, holes etc) but also the vitreoretinal interface, such as persistent vitreoretinal attachments and tractions on the retina. The use of a circular concave mirror, or preferably an elliptical mirror, permits us to place the focal point (or the second focal point of an elliptical mirror) at the pupil or further in a posterior plane inside the eye permitting the scan to pass with ease through a small pupil while larger area of the retina are being scanned. The central part of these mirrors can also be replaced by a transparent glass so that a central OCT scan can be obtained initially from limited central area. (FIG. 3 A, B, C). As soon as an image is obtained from the retina the central part of the mirror can be replaced automatically by the second scanner reflecting the light off the concave mirror and scanning and acquisition is obtained from this separate line which gives a wide angle OCT, imaging including the entire retina.

After positioning the patient's head in front of a head holder, used for fundus photography, the OCT system can be moved toward the eye. Once the retina is visualized with the infrared beam through the central (transparent) part of the concave mirror, the central part can be switched with equal size mirror and the other arm of the OCT system can be activated which records rapidly a circular field of 120-200 degree, depending on the mirror used. Alternatively, the central part can also be made with a partial reflecting mirror which would eliminate actual physical exchange of the central part. The data collected can be analyzed and compared with ophthalmoscopic examinations and fundus photography done on each patient. Embodiments of the present invention are also capable of providing a black and white fundus picture. The scan can be modified to provide a false color image of the retina and its interface. The OCT according to embodiments of the present invention is not only capable of providing a cross sectional view of the entire area including the Optic Nerve head, Vitreoretinal adhesions, but also can provide an elevation map of the scanned field. The information gained is invaluable for decision making prior to vitreoretinal surgery, and laser application in patients with diabetic retinopathy, macular degeneration, glaucoma, inherited retinal degeneration, retinal diseases predisposing to a retinal detachment etc.

The same system can be used for obtaining wide angle OCT of the cornea and the anterior segment of the eye including the lens by moving the mirror away from the eye.

Figure 5:
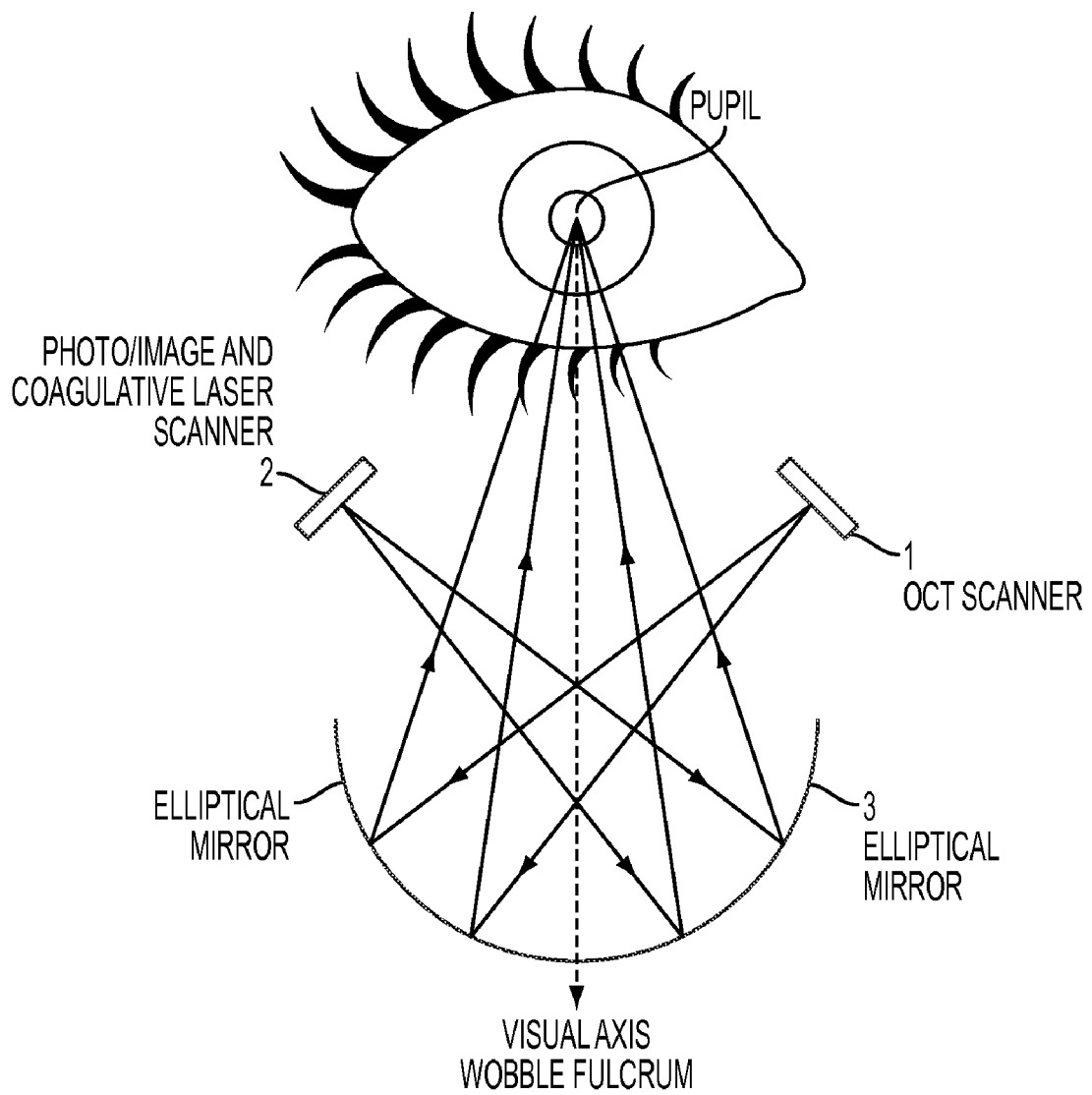
FIG. 5 illustrates an embodiment of the present invention that includes two scanners.

As shown in FIG. 5, another embodiment of the present can include a second scanner. In this embodiment, the second scanner is capable of emitting a white light source for digital photography of the retina (or the cornea, depending on the position of the mirror's secondary focal point). The second scanner is also capable of storing and processing information obtained and presenting the information in 2D or 3D format on a computer screen.

Additionally, in one embodiment, the scanner is equipped with multiple laser beams to obtain an image of the retina with three compensatory colors, green, red, and blue or infrared, if desired. A filter that is 500 nm, along with the blue wave length can be used for flouorescein angiography or another filter at 800 nm for indicyanin green angiography. These diagnostic images can be transmitted, as is known in the art, to a fundus camera etc. and digital image can be stored. The images can be presented on a touch screen monitor to evaluate specific area of the fundus using diagnostic photos, superimposed on the OCT images; obtained from the OCT scanner using an image processor, creating 2-3 D images of any part of the central and/or peripheral retina, etc., which can be selected on the touch screen monitor and can be used to demonstrate the cornea, anterior chamber or the lens in 2-3D format.

In another embodiment, the second scanner is equipped with at least one or more high power lasers (elecrtomagnetic waves) having wavelengths of about 192 nm to 3.9 micron. The lasers are capable of producing the rise of the tissue temperature to the desired hyperthermic effect, coagulative or photoablative effect. Moreover, the second scanner can be armed with one or more powerful coagulative lasers (having different wave lengths) to apply scatter laser lesions in the retina.

In one embodiment the areas to be coagulated can be selected on the touch screen monitor having 2-3 D format, which results in applying very short pulses of laser delivered in a short time to cover a part or all of the retina except for the macula area.

Furthermore, the desired area of the retina or the cornea can be marked on the touch sensitive screen, including or excluding an area from the thermal effect, ablative effects of the laser.

Additionally, in one embodiment, the invention is capable of remote recording and transmission of the information, via the internet or any other suitable transmission medium. Thus, the person performing the procedure can be located in a different locale, or multiple people in various locations can watch and/or assist in the procedure.

In another embodiment, an ultrasonic arrays transducer can placed on the lid for producing and receiving ultrasonic pulse of 500 Hz-80 MHz, which can be useful for acoustic spectroscopy and data storage for creating a 2-3 D format of the photoacoustic image of an area.

In such an embodiment, the invention would be capable of recording photoacoustic information at 100-10 MHz where a heat energy creates a photo-acoustic sound capable of measuring of the tissue temperature rise after laser application and a means or device cable of connecting and controlling the desired thermal effect using computer software that gives feed back to the laser to maintaining the desired tissue temperature by modifying instantly the laser energy level per pulse.

In one embodiment a third scanner/laser can be used. In this embodiment, the second laser can, for example, emit white light, and the third laser enables a rise in tissue temperature to the desired hyperthermic, coagulative and/or photoablative effect.

In each of the embodiments discussed above, one of a concave mirror or an elliptical mirror having an axis extending through a central portion thereof, is configured to repeatedly oscillate or wobble between a first position and a second position around the axis, so as to record a field of up to 200 degrees of a portion of the central and peripheral retina. If desired a central portion of the mirror (e.g., about 1 mm to 6 mm, and preferably about 5 mm) can be disconnected, so as to oscillate relative to the remainder of the mirror. The oscillation speed can vary depending on the speed selected by the person performing the procedure.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A system for imaging of the central and peripheral retina, comprising:
   one of a concave mirror and an elliptical mirror having an axis extending through a central portion thereof, and at least a portion of said one of a concave mirror and an elliptical mirror being configured to repeatedly oscillate between a first position and a second position around the axis, so as to record a field of up to 200 degrees of a portion of the central and peripheral retina;
   a first scanner configured to use a spectral domain optical coherence tomography system to obtain a non-contact wide angle optical coherence tomography-image of the portion of the central and peripheral retina; and
   a second scanner configured to obtain an image of the retina,
   wherein the one of a concave mirror and an elliptical mirror is configured to oscillate so as to move the focal point of the one of a concave mirror and an elliptical mirror from one side of a pupil to another side, thereby permitting scanning light inside the eye to cover a predetermined peripheral field, thus creating a two dimensional or three dimensional image of the field.

2. A system according to claim 1, wherein
   said second scanner is configured to emit white light capable of digital photography.

3. A system according to claim 1, wherein
said second scanner includes a first, second and third laser beam capable of obtaining an image using green, red and blue light, respectively.

4. A system according to claim 3, wherein
said second scanner includes a 500 nm filter for the blue light and a 800 nm filter for the green light.

5. A system according to claim 1, wherein
said second scanner includes a laser capable of emitting electromagnetic waves having a wavelength between about 192 nm to about 3.9 microns.

6. A system according to claim 1 wherein
said second scanner is configured to produce a rise in temperature so as to create a hyerthermic, coagulative or photoablative effect.

7. A system according to claim 1, further comprising
a touch screen display device configured to display a desired area of the fundus.

8. A system according to claim 1, wherein
a device configured to transmit the two dimensional or three dimensional image of the field to a separate location.

9. A system according to claim 1, further comprising
an ultrasonic array transducer configured to by placed on an eyelid and produce and receive ultrasonic pulses so as to be useful in acoustic spectroscopy and data storage for creating the two dimensional or three dimensional image.

10. A system according to claim 9, wherein
said ultrasonic transducer is configured to record photoacoustic information at 100-10 MHz where heat energy creates a photoacoustic sound capable of measuring of the tissue temperature rise after laser application and configured to connect and control a thermal effect using computer software that gives feed back to the second scanner to maintain a desired tissue temperature by modifying the laser energy level per pulse.

11. A system according to claim 1, wherein
said at least a portion of said one of a concave mirror and an elliptical mirror is a central portion.

12. A method for imaging of the central and peripheral retina, comprising:
repeatably oscillating at least a portion of one of a concave mirror and an elliptical mirror between a first position and a second position around an axis extending through a central portion of the one of a concave mirror and an elliptical mirror, so as to record a field of up to 200 degrees of a portion of the central and peripheral retina,
obtaining a non-contact wide angle optical coherence tomography-image of a portion of the central and peripheral retina via a scanner using a spectral domain optical coherence tomography system using a first scanner, and
obtaining a digital image of the retina using a second scanner,
wherein the oscillating one of a concave mirror and an elliptical mirror around an axis includes oscillating the one of a concave mirror and an elliptical mirror around the axis so as to move the focal point of the mirror from one side of a pupil to another side, thereby permitting scanning light inside the eye to cover a predetermined peripheral field, thus creating a two dimensional or three dimensional image of the field.

13. A method according claim 12, said second scanner emits white light capable of digital photography or emits green, red and blue light.

14. A method according to claim 13, further comprising
filtering the blue light with a 500 nm filter and filtering the green light with a 800 nm filter.

15. A method according to claim 12, wherein
emitting electromagnetic waves having a wavelength between about 192 nm to about 3.9 microns using a laser in the second scanner.

16. A method according to claim 12, further comprising
displaying a desired area of the fundus on a touch screen display device.

17. A method according to claim 12, further comprising
transmitting the two dimensional or three dimensional image of the field to a separate location.

18. A method according to claim 12, further comprising
placing an ultrasonic array transducer on an eyelid and to produce and receive ultrasonic pulses so as to be useful in acoustic spectroscopy and data storage for creating the two dimensional or three dimensional image.

19. A method according to claim 18, wherein
said ultrasonic transducer records photoacoustic information at 100-10 MHz where heat energy creates a photoacoustic sound capable of measuring of the tissue temperature rise after laser application and configured to connect and control a thermal effect using computer software that gives feed back to the second scanner to maintain a desired tissue temperature by modifying the laser energy level per pulse.

20. A method according to claim 12, wherein
said oscillating at least a portion of said one of a concave mirror and an elliptical mirror includes oscillating a central portion of said one of a concave mirror and an elliptical mirror.

* * * * *